US009175041B2

(12) United States Patent  
Pettit et al.

(10) Patent No.: US 9,175,041 B2
(45) Date of Patent: Nov. 3, 2015

(54) CRYSTAL STRUCTURES OF DOLASTATIN 16, DOLAMETHYLLEUINE AND DOLAPHENVALINE, AND METHODS FOR PREPARING DOLAMETHYLLEUINE AND DOLAPHENVALINE

(75) Inventors: George R. Pettit, Paradise Valley, AZ (US); Thomas Smith, Tempe, AZ (US); Jun-Ping Xu, Chandler, AZ (US); Delbert Herald, Tempe, AZ (US)

(73) Assignee: Arizona Board of Regents, a body corporate of the State of Arizona, acting for and on behalf of Arizona State University, Scottsdale, AZ (US)

( * ) Notice: Subject to any disclaimer, the term of this patent is extended or adjusted under 35 U.S.C. 154(b) by 81 days.

(21) Appl. No.: 14/113,682

(22) PCT Filed: Apr. 25, 2012

(86) PCT No.: PCT/US2012/034859
§ 371 (c)(1),
(2), (4) Date: Feb. 4, 2014

(87) PCT Pub. No.: WO2012/148943
PCT Pub. Date: Nov. 1, 2012

(65) Prior Publication Data
US 2014/0179897 A1 Jun. 26, 2014

Related U.S. Application Data

(60) Provisional application No. 61/478,866, filed on Apr. 25, 2011.

(51) Int. Cl.
*C07K 7/54* (2006.01)
*C07K 5/02* (2006.01)
*C07C 227/18* (2006.01)
*G06F 19/00* (2011.01)
*A61K 38/00* (2006.01)

(52) U.S. Cl.
CPC ............... *C07K 7/54* (2013.01); *C07C 227/18* (2013.01); *C07K 5/0205* (2013.01); *G06F 19/701* (2013.01); *A61K 38/00* (2013.01)

(58) Field of Classification Search
None
See application file for complete search history.

(56) References Cited

U.S. PATENT DOCUMENTS

| 5,554,725 A * | 9/1996 | Pettit ............................. 530/330 |
| 6,239,104 B1 * | 5/2001 | Pettit et al. ..................... 514/19.2 |
| 2003/0101005 A1 * | 5/2003 | Muller-Dieckmann et al. ............................. 702/27 |
| 2004/0204862 A1 | 10/2004 | Wainer et al. | |

OTHER PUBLICATIONS

Benvenuti et al. "Crystallization of soluble proteins in vapor diffusion for x-ray crystallography," Nature Protocols, 2007, vol. 2. No. 2, 1633-1651.*
Cudney "Protein Crystallization and Dumb Luck" The Rigaku Journal 1999, vol. 16. No. 1, 1-7.*
Drenth "Crystallizing a Protein" in Principles of Protein X-Ray Crystallography,1999, 2nd Edition.*
Kundrot "Which strategy for a protein crystallization project?" CMLS, Cell. Mol. Life Sci., 2004, vol. 61, 525-536.*
McPherson "Current Approaches to Macromolecular Crystallization," Eur. J. Biochem, 1990, vol. 189, 1-23.*
Bis et al. "Defining & Addressing Solid-State Risks After the Proof-of-Concept Stage of Pharmaceutical Development," Drug Development & Delivery, Apr. 2011, pp. 32-34.*
Adams, et al., Isolation and Structure Determination of Malevamide E, a Dolastatin 14 Analogue, from the marine cyanobacterium Symploca laete-veridis, Journal of Natural Products, 2008, vol. 71, pp. 750-754.
Duboudin, et al., Reactifs de grignard vinyliques fonctionnels, Journal of Organometallic Chemistry, 1979, vol. 168, pp. 1-11, Elsevier Sequoia S.A., Netherlands.
Gunasekera, et al., Molassamide, a depsipeptide serine protease inhibitor from the marine cyanobacterium Dichothrix utahensis, Journal of Natural Products, 2010, vol. 73, pp. 459-462.
Harrigan, et al., Isolation, structure determination, and biological activity of dolastatin 12 and lyngbyastatin 1 from Lyngbya majuscula/Schizothrix calcicola cyanobacterial assemblages, Journal of Natural Products, 1998, vol. 61, pp. 1221-1225.
Keck, et al., Total synthesis of epothilones B and D: stannane equivalents for beta-keto ester dianions, Journal of Organic Chemistry, Dec. 2008, vol. 73, No. 24, pp. 9675-9691.
Kimura, et al., Kulokekahilide-1, a cytotoxic depsipeptide from the cephalaspidean mollusk *Philinopsis speciosa*, Journal of Organic Chemistry, 2002, vol. 67, pp. 1760-1767, American Chemical Society.
Kingston, Tubulin-interactive natural products as anticancer agents, Journal of Natural Products, Mar. 2009, vol. 72, No. 3, pp. 507-515.
Lau, et al., Reductive deoxygenation of aryl aldehydes and ketones and benzylic, allylic, and tertiary alcohols by ZnI2—NaCNBH3, Journal of Organic Chemistry, 1986, vol. 51, pp. 3038-3043, American Chemical Society.
Luesch, et al., Isolation of dolastatin 10 from the marine cyanobacterium *Symploca* species VP642 and total stereochemistry and biological evaluation of its analogue symplostatin 1, Journal of Natural Products, 2001, vol. 64, pp. 907-910.
Mehta, et al., Improved efficiency and selectivity in peptide synthesis: use of triethylsilane as a carbocation scavenger in deprotection of t-butyl esters and t-butoxycarbonyl-protected sites, Tetrahedron Letters, 1992, vol. 33, No. 37, pp. 5441-5444, Pergamon Press Ltd., Great Britain.

(Continued)

*Primary Examiner* — Christina Bradley
(74) *Attorney, Agent, or Firm* — Byrne Poh LLP; Nina R. Horan (57) ABSTRACT

The present invention relates to the crystal structures of dolastatin 16, dolamethylleuine and dolaphenvaline. The present invention also relates to processes for preparing dolamethylleuine and dolaphenvaline. The present invention further relates to computer readable medium with crystal structural data and/or information stored thereon.

4 Claims, 3 Drawing Sheets

(56) References Cited

OTHER PUBLICATIONS

Nogle, et al., Somamides A and B, two new depsipeptide analogues of dolastatin 13 from a Fijian cyanobacterial assemblage of *Lyngbya majuscula* and *Schizothrix* species, Journal of Natural Products, 2001, vol. 64, pp. 716-719.

Nogle, et al., Isolation of four new cyclic depsipeptides, antanapeptins A-D, and dolastatin 16 from a Madagascan collection of *Lyngbya majuscula*, Journal of Natural Products, 2002, vol. 65, pp. 21-24.

Paterson, et al., Total synthesis of cytotoxic marine macrolides: Callipelto A, aurisides A and B, and dolastatin 19, Pure Applied Chemistry, 2008, vol. 80, No. 8, pp. 1773-1782, IUPAC.

Pettit, et al., Antineoplastic agents. 570. Isolation and structure elucidation of bacillistatins 1 and 2 from a marine *Bacillus silvestris*, Journal of Natural Products, Mar. 2009, vol. 72, No. 3, pp. 366-371.

Pettit, et al., Isolation and structure of the human cancer cell growth inhibitory cyclodepsipeptide dolastatin 16, Journal of Natural Products, 1997, vol. 60, pp. 752-754.

Prokopiou, et al., Potentiation of the activity of cisplatin in a human colon tumour xenograft model by auristatin PYE, a structural modification of dolastatin 10, Molecular Medicine Reports, 2010, vol. 3, pp. 309-313.

Seebach, et al., Alpha-alkylation of beta-aminobutanoates with lk-1. 2-induction, Tetrahedron Letters, 1987, vol. 28, No. 27, pp. 3103-3106, Pergamon Journals Ltd., Great Britain.

Taber, et al., Convenient preparation of tert-butyl esters, Tetrahedron Letters, 2006, vol. 47, pp. 3065-3066, Elsevier Ltd.

Taori, et al., Combinatorial strategies by marine cyanobacteria: symplostatin 4, an antimitotic natural dolastatin 10/15 hybrid that synergizes with the coproduced HDAC inhibitor largazole, ChemBioChem, 2009, 1634-1639.

Woyke, et al., Effect of auristatin PHE on microtubule integrity and nuclear localization in *Cryptococcus neoformans*, Antimicrobial Agents and Chemotherapy, Dec. 2002, vol. 46, No. 12, pp. 3802-3808, American Society for Microbiology.

Woyke, et al., Differential gene expression in auristatin PHE-treated *Cryptococcus neoformans*, Antimicrobial Agents and Chemotherapy, Feb. 2004, vol. 48, No. 2, pp. 561-567, American Society for Microbiology.

Kazmaier, et al., Asymmetric chelated claisen rearrangements in the presence of chiral ligands—scope and limitations, Chemistry: A European Journal, 2002, vol. 8, No. 8, pp. 1850-1855.

Mues, et al., The asymmetric chelate-claisen rearrangement as a key step in the synthesis of non-proteinogenic amino acids, Synthesis, 2001, pp. 487-498.

Hirai, et al., Studies on the novel cyclodepsipeptides. A total synthesis of (+)-Jasplakinolide (jaspamide), Heterocycles, 1994, vol. 39, pp. 603-612.

Paterson, et al., Recent advances in the total synthesis of polyketide natural products as promising anticancer agents, Australian Journal of Chemistry, 2009, vol. 62, pp. 624-638.

Podlech, et al., On the preparation of β-amino acids from α-amino acids using the Arndt-Eistert reaction: Scope, limitations and stereoselectivity. Application to carbohydrate peptidation. Stereoselective α-alkylations of some β-amino acids, Liebigs Annalen, 1995, pp. 1217-1228.

Singh, et al., Clinical status of anti-cancer agents derived from marine sources, Anti-cancer Agents in Medicinal Chemistry, 2008, vol. 8, No. 6, pp. 603-617.

Pettit et al., Antineoplastic Agents. 590. The X-ray crystal structure of dolastatin 16 and syntheses of the dolamethylleuine and dolaphenvaline units, Journal of Natural Products, May 2011, vol. 74, No. 5, pp. 1003-1008.

International Preliminary Report on Patentability in International Application No. PCT/US2012/034859, filed Apr. 25, 2012, mailed Nov. 7, 2013.

International Search Report and Written Opinion dated Sep. 27, 2012 in International Patent Application No. PCT/US2012/034859.

Pettit, G.R., "Dolastatin Anticancer Drugs", In International Oncology Updates: Marine Anticancer Compounds in the Era of Targeted Therapies, 2009, pp. 19-49.

Pettit, G.R., "The Dolastatins", In Progress in the Chemistry of Organic Natural Products, vol. 70, 1997, pp. 2-70.

* cited by examiner

CRYSTAL STRUCTURES OF DOLASTATIN 16, DOLAMETHYLLEUINE AND DOLAPHENVALINE, AND METHODS FOR PREPARING DOLAMETHYLLEUINE AND DOLAPHENVALINE

CROSS REFERENCE TO RELATED APPLICATIONS

This application claims the benefit U.S. Provisional Application No. 61/478,866, filed Apr. 25, 2011, which is incorporated by reference herein in its entirety.

FEDERALLY SPONSORED RESEARCH OR DEVELOPMENT

This invention was made with government support from grant R01 CA090441 awarded by the National Institute of Health. The government has certain rights in the invention.

FIELD OF THE INVENTION

The present invention relates to the crystal structures of dolastatin 16, dolamethylleuine and dolaphenvaline. The present invention also relates to processes for preparing dolamethylleuine and dolaphenvaline. The present invention further relates to computer readable media having crystal structural data and/or information stored thereon.

BACKGROUND OF THE INVENTION

Very early in the discovery of the biologically remarkable and structurally unique peptides from the sea hare *Dolabella auricularia*, which have been designated dolastatins, it became clear that certain members (e.g. 10-15) exhibited a variety of important properties that include anticancer (Pettit, G. R. In *International Oncology Updates: Marine anticancer compounds in the era of targeted therapies*; Chabner, B.; Cortés-Funes, H., Eds.; Permanyer Publications: Barcelona, 2009; Kingston, D. G. I. *J. Nat. Prod.* 2009, 72, 507-515; Singh, R.; Sharma, M.; Joshi, P.; Rawat, D. S. *Anti-Cancer Agents Med. Chem.* 2008, 8, 603-617; Pettit, G. R. In *Progress in the Chemistry of Organic Natural Products*; Herz, W.; Kirby, G. W.; Moore, R. E.; Steglich, W.; Tamm, C., Eds.; Springer: Vienna, 1997; Vol. 70, 1-79) and antifungal activities (Woyke, T.; Roberson, R. W.; Pettit, G. R.; Winkelmann, G.; Pettit, R. K. *Antimicrob. Agents Chemother.* 2002, 46, 3802-3808; Woyke, T.; Berens, M. E.; Hoelzinger, D. B.; Pettit, G. R.; Winkelmann, G.; Pettit, R. K *Antimicrob. Agents Chemother.* 2004, 48, 561-567). Indeed, dolastatin 10 and three structural modifications are currently in human cancer phase II and phase III clinical trials (Pettit, G. R. In *International Oncology Updates: Marine anticancer compounds in the era of targeted therapies*; Chabner, B.; Cortés-Funes, H., Eds.; Permanyer Publications: Barcelona, 2009). Two derivatives of dolastatin 15 are also in cancer clinical trials (phase I-II) (Pettit, G. R. In *International Oncology Updates: Marine anticancer compounds in the era of targeted therapies*; Chabner, B.; Cortés-Funes, H., Eds.; Permanyer Publications: Barcelona, 2009).

When the present inventors extended the field collections of *D. auricularia* from the Indian Ocean to the Western Pacific (Papua New Guinea and the Philippines), the dolastatin series was expanded to dolastatin 16-19 (Pettit, G. R.; Xu, J.-p.; Hogan, F.; Williams, M. D.; Doubek, D. L.; Schmidt, J. M.; Cerny, R. L.; Boyd, M. R. *J. Nat. Prod.* 1997, 60, 752-754; Paterson, I.; Findlay, A. D. *Aust. J. Chem.* 2009, 62, 624-638; Paterson, I.; Findlay, A. D. *Pure Appl. Chem.* 2008, 80, 1773-1782). Dolastatin 16, shown below as compound 1, especially proved to be an exceptionally potent inhibitor of cancer cell growth and a candidate for further development (Pettit, G. R.; Xu, J.-p.; Hogan, F.; Williams, M. D.; Doubek, D. L.; Schmidt, J. M.; Cerny, R. L; Boyd, M. R. *J. Nat. Prod.* 1997, 60, 752-754).

1

Structurally, dolastatin 16 is a cyclodepsipeptide containing two new amino acids, dolamethylleuine (Dml, 2), a β-amino acid, and dolaphenvaline (Dpv, 3). The structure of dolastatin 16 without assignment of the configuration of the novel amino acids was achieved by high-field NMR and tandem MS/MS mass spectroscopic interpretations (Pettit, G. R.; Xu, J.-p.; Hogan, F.; Williams, M. D.; Doubek, D. L.; Schmidt, J. M.; Cerny, R. L.; Boyd, M. R. *J. Nat. Prod.* 1997, 60, 752-754).

Development of dolastatin 16 as an anticancer agent has been delayed for two reasons. First, dolastatin 16 was originally isolated in low yield (in $3.1 \times 10^{-7}\%$ yield) as an amorphous powder. Second, long period of attempts at crystallization were unsuccessful. Thus, to develop dolastatin 16, there is a need for unequivocal configurational assignments and a practical total synthesis for scale-up production.

Other options for obtaining certain dolastatin members appeared likely some 35 years ago when considering the fact that *Dolabella* species derived nutrition by consuming marine microalgae and that such exogenous sources might provide the dolastatins or intermediates (Pettit, G. R. In *Progress in the Chemistry of Organic Natural Products*; Herz, W.; Kirby, G. W.; Moore, R. E.; Steglich, W.; Tamm, C., Eds.; Springer: Vienna, 1997; Vol. 70, 1-79). This expectation has been amply realized over the past decade by the isolation of dolastatins 10-16 or close analogues from the cyanobacterium *Lyngbya majuscula* and other such microalgae (Pettit, G. R.; Xu, J.-p.; Hogan, F.; Williams, M. D.; Doubek, D. L.; Schmidt, J. M.; Cerny, R. L.; Boyd, M. R. *J. Nat. Prod.* 1997, 60, 752-754; Luesch, H.; Moore, R. E.; Paul, V. J.; Mooberry, S. L.; Corbett, T. H. *J. Nat. Prod.* 2001, 64, 907-910; Harrigan G. G.; Yoshida, W. Y.; Moore, R. E.; Nagle, D. G.; Park, P. U.; Biggs, J.; Paul, V. J.; Mooberry, S. L.; Corbett, T. H.; Valeriote, F. A. *J. Nat. Prod.* 1998, 61, 1221-1225; Nogle, L. M.; Williamson, R. T.; Genvick, W. H. *J. Nat. Prod.* 2001, 64, 716-719; Gunasekera, S. P.; Miller, M. W.; Kwan, J. C.; Luesch, H.; Paul, V. J. *J. Nat. Prod.* 2010, 73, 459-462; Adams, B.; Pörzgen, P.; Pittman, E.; Yoshida, W. Y.; Westenburg, H. E.; Horgen, F. D. *J. Nat. Prod.* 2008, 71, 750-754; Taori, K.; Liu, Y.; Paul, V. J.; Luesch, H. *Chem Bio Chem*

2009, 10, 1634-1639; Nogle, L. M.; Genvick, W. H. *J. Nat. Prod.* 2002, 65, 21-24). Thus, fermentation methods using marine cyanobacteria may eventually be competitive with total syntheses for scale-up production of new anticancer drugs in the family. At present, the yields from these initial experiments remain very low, and for the foreseeable future the provision of dolastatin 16 for cancer clinical trial development will require a practical total synthesis for scale-up production.

SUMMARY OF THE INVENTION

Thus, the present invention provides, for the first time, the crystal structure of dolastatin 16. Solving this crystal structure has allowed for unequivocal configurational assignments, and for the identification and syntheses of two new amino acids, dolamethylleuine and dolaphenvaline.

The present invention provides a crystallizable composition, crystal, and the crystal structure of dolastatin 16. Dolastatin 16 has the following chemical structure:

1

The present invention provides a method for obtaining a crystal of dolastatin 16.

The present invention also provides a method for preparing Z-dolamethylleuine. Dolamethylleuine has the following chemical structure:

2

The present invention provides a crystallizable composition, crystal, and the crystal structure of Z-dolamethylleuine.

The present invention provides a method for obtaining a crystal of Z-dolamethylleuine.

The present invention further provides a method for preparing TFA-dolaphenvaline. Dolaphenvaline has the following chemical structure:

3

The present invention provides a crystallizable composition, crystal, and the crystal structure of TFA-dolaphenvaline.

The present invention provides a method for obtaining a crystal of TFA-dolaphenvaline.

The present invention also provides a non-transitory computer readable medium having crystal structural data and/or information stored thereon. The crystal structure data and/or information may be those of dolastatin 16, Z-dolamethylleuine or TFA-dolaphenvaline.

The present invention also provides a computer system comprising a computer readable medium of the present invention.

The present invention further provides a method of designing analogs of dolastatin 16 using a computer system of the present invention.

DETAILED DESCRIPTION OF THE INVENTION

In order that the invention herein described may be fully understood, the following detailed description is set forth.

Unless defined otherwise, all technical and scientific terms used herein have the same meaning as those commonly understood by one of ordinary skill in the art to which this invention belongs. Although methods and materials similar or equivalent to those described herein can be used in the practice or testing of the present invention, suitable methods and materials are described below. The materials, methods and examples are illustrative only, and are not intended to be limiting. All publications, patents, hyperlinks, and other documents mentioned herein are incorporated by reference in their entirety.

Throughout this specification, the word "comprise" or variations such as "comprises" or "comprising" will be understood to imply the inclusion of a stated integer or groups of integers but not the exclusion of any other integer or group of integers.

The term "a" or "an" may mean more than one of an item.

The terms "and" and "or" may refer to either the conjunctive or disjunctive and mean "and/or".

The term "about" means within plus or minus 10% of a stated value. For example, "about 100" would refer to any number between 90 and 110. The term "about" when used in the context of root mean square deviation (RMSD) values takes into consideration the standard error of the RMSD value, which is +/−0.1 Å.

Additional definitions are set forth in the specification, where necessary.

X-Ray Structural Determination of Dolastatin 16

In one embodiment, the present invention provides a crystallizable composition or a crystal comprising dolastatin 16. In another embodiment, the crystal has a unit cell dimension of a=10.844 (5) Å, b=16.133 (5) Å, c=16.050 (5) Å, α=90.000 (5)°, β=104.062 (5)°, γ=90.000 (5)°, V=2720.4 (17) Å$^3$ and belongs to space group P2(1). It will be readily apparent to those skilled in the art that the unit cells of the crystal compositions may deviate +/−1-2 Å from the above cell dimensions depending on the deviation in the unit cell calculations.

Figure 1:
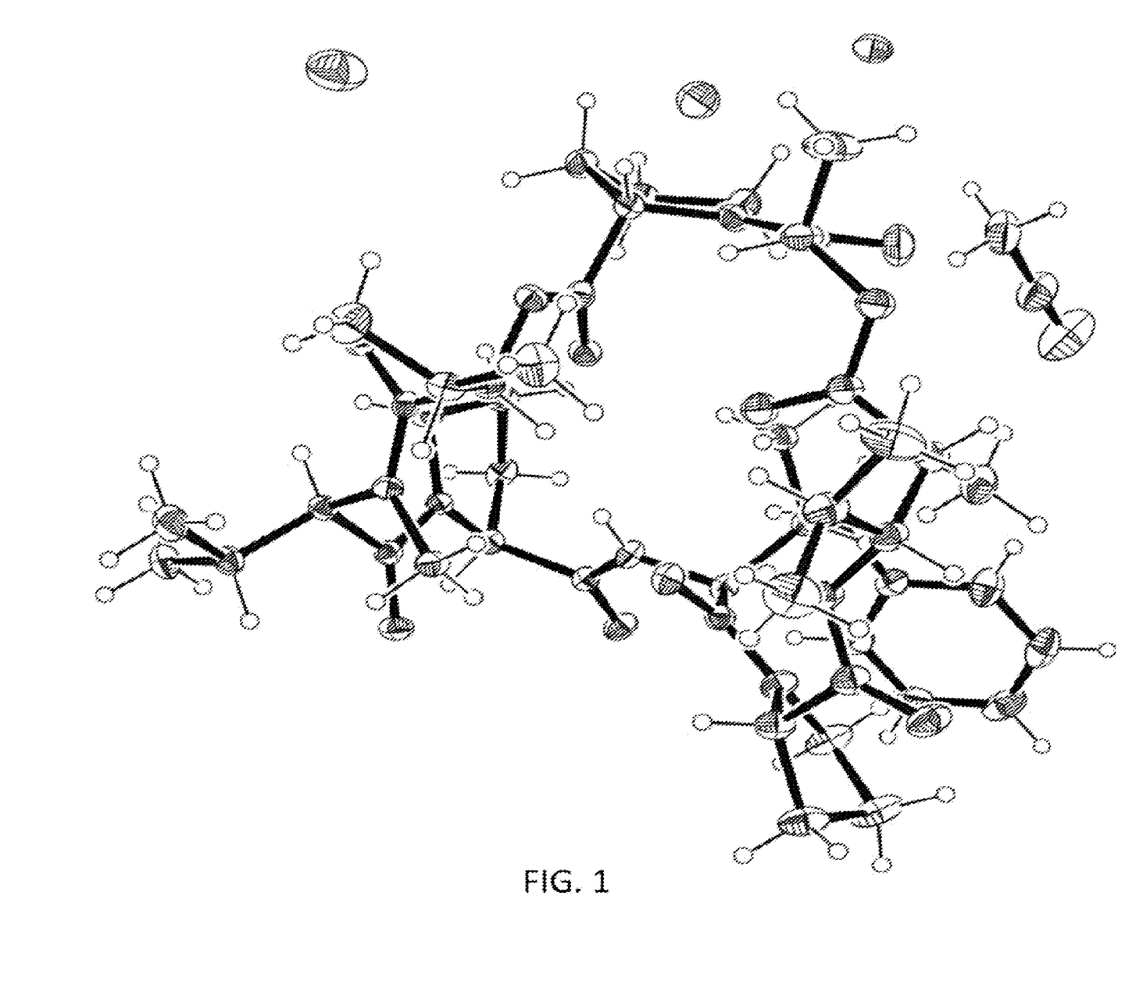
FIG. 1 is an X-ray structure of dolastatin 16. The atoms of this cyclic depsipeptide and solvent (one acetonitrile and three water) molecules are displayed as 30% probability thermal ellipsoids.

The crystal structure of dolastatin 16 is presented in FIG. 1. X-ray crystallographic analysis of dolastatin 16 confirmed it has a cyclodepsipeptide structure containing two new amino acids, dolamethylleuine (Dml, 2), a β-amino acid, and dolaphenvaline (Dpv, 3). In addition, the X-ray crystallographic analysis has permitted the configurational assignments of the new amino acids as 2R, 3R for dolamethylleuine and 2S, 3R for dolaphenvaline as shown in FIG. 1.

The present invention also provides a method for obtaining a crystal of dolastatin 16. The method comprises the steps of:

(a) combining dolastatin 16 with a crystallization solution to produce a crystallizable composition; and (b) subjecting the crystallizable composition to conditions that promote crystallization, thereby obtaining said crystal.

The crystallization solution comprises acetonitrile and water.

According to one embodiment, the crystallizable composition comprises dolastatin 16. Dolastatin 16 may be obtained from natural sources or by synthetic methods. Dolastatin 16 is preferably about 85% to about 100% pure prior to forming the crystallizable composition. More preferably, dolastatin 16 is about 90% to about 100% pure. Even more preferably, dolastatin 16 is about 95% to about 100% pure.

Conditions that promote crystallization are known to those of skill in the art and include, but are not limited to, pH, ionic strength, temperature, dolastatin 16 concentration, the presence of various salts, ligands or additives, the type of precipitant and the actual crystallization method (hanging drop, sitting drop, dialysis, etc.).

The crystallizable composition is left to stand at about 0° C. for a time equal to or greater than 1 year, preferably approximately ranging from 1 to 4 years. In preferred embodiments to obtain X-ray quality crystals, the time is over three years.

It would be readily apparent to one of skill in the art to vary the crystallization conditions disclosed above to identify other crystallization conditions that would produce crystals of dolastatin 16. Such variations include, but are not limited to, adjusting pH, concentration and/or crystallization temperature, introducing a salt and/or precipitant, using a device for promoting crystallization, microseeding, using a different method for crystallization, or introducing additives such as detergents (e.g., TWEEN® 20 (monolaurate), LDOA, BRIJ® 30 (4 lauryl ether)), sugars (e.g., glucose, maltose), organic compounds (e.g., dioxane, dimethylformamide), lanthanide ions, or poly-ionic compounds that aid in crystallizations. High throughput crystallization assays may also be used to assist in finding or optimizing the crystallization condition.

In some embodiments, the method for obtaining a crystal of dolastatin 16 further comprises isolating the resulting crystals from the crystallizable composition. The crystals may be isolated by any conventional means, such as filtration, concentration, centrifugation, and the like.

Process for Preparing Z-Dolamethylleuine and X-ray Structural Determination of the Same The present invention provides a process for preparing Z-dolamethylleuine:

The method comprises the steps of:

(a) converting benzyloxy-carbonyl valine 4 to a diazoketone 5:

(b) converting diazoketone 5 to ester 6:

(c) converting ester 6 to α-methylated ester 7:

and
(d) deprotecting α-methylated ester 7 to make Z-dolamethylleuine:

In step (a), benzyloxy-carbonyl valine 4 is converted to diazoketone 5 using the Arndt-Eistert reaction, namely, by converting benzyloxy-carbonyl valine 4 to an acid chloride and reacting the acid chloride with a diazomethane compound. Methods for converting a carboxylic acid (such as benzyloxy-carbonyl valine 4) are known in the art and any such method can be used. Diazomethane compounds are known in the art and any such diazomethane compound can be used. Preferably, the diazocompound is trimethylsilyldiazomethane.

In step (b), diazoketone 5 is converted to ester 6 via a Wolff rearrangement catalyzed by a silver salt to give a reactive carbene that is reacted with tert-butanol to afford the ester 6. Silver salts are known in the art and any such salt may be used. Preferably, the silver salt is a benzoic acid salt.

In step (c), ester 6 is converted to α-methylated ester 7 by reaction with a methylating agent and a base. Methods for methylating the α-position of esters are known in the art and any such method may be used. Preferably, the methylation reaction is accomplished stereoselectively. More preferably, the methylating reaction uses iodomethane, lithium chloride (LiCl) and lithium diisopropylamide (LDA).

In step (d), the α-methylated ester 7 is deprotected to provide Z-dolamethylleuine. Methods for deprotecting tert-butyl esters are known in the art and any such method may be used. See, e.g., Greene, T. W., Wuts, P. G in "Protective Groups in Organic Synthesis," Third Edition, John Wiley & Sons, New York: 1999, and other editions of this book. Preferably, the deprotection reaction uses trifluoroacetic acid (TFA) and triethylsilane (TES).

Scheme 1 depicts a preferred process of the present invention.

The steps illustrated in Scheme 1 may be described as follows. With Z—R-valine 4 as substrate, the Arndt-Eistert reaction (Podlech, J.; Seebach, D. Liebigs Ann. 1995, 1217-1228) followed by a Wolff rearrangement (Hirai, Y.; Yokota, K.; Momose, T. Heterocycles 1994, 39, 603-612) of the resulting diazoketone 5 afforded the protected β-amino acid 6. Methylation at the α-position was accomplished stereoselectively with LDA and iodomethane to afford 7 (Podlech, J.; Seebach, D. Liebigs Ann. 1995, 1217-1228; Hirai, Y.; Yokota, K.; Momose, T. Heterocycles 1994, 39, 603-612; Seebach, D.; Estermann, H. Tetrahedron Lett. 1987, 28, 3103-3106). Deprotection of the tert-butyl ester by use of trifluoroacetic acid (TFA) and triethylsilane (TES) in methylene chloride provided Z-Dml 8 (Mehta, A.; Jaouhari, R.; Benson, T. J.; Douglas, K. T. Tetrahedron Lett. 1992, 33, 5441-5444).

In one embodiment, the present invention provides a crystallizable composition or a crystal comprising Z-dolamethylleuine. In another embodiment, the crystal is in space group P2(1); and said crystal has unit cell dimensions of a=7.2182 (2) Å, b=8.5374 (3) Å, c=12.1649 (4) Å, α=90.00°, β=99.722 (2)°, γ=90.00°, V=738.89 (4) Å$^3$. It will be readily apparent to those skilled in the art that the unit cells of the crystal compositions may deviate +/−1-2 Å from the above cell dimensions depending on the deviation in the unit cell calculations.

Figure 2:
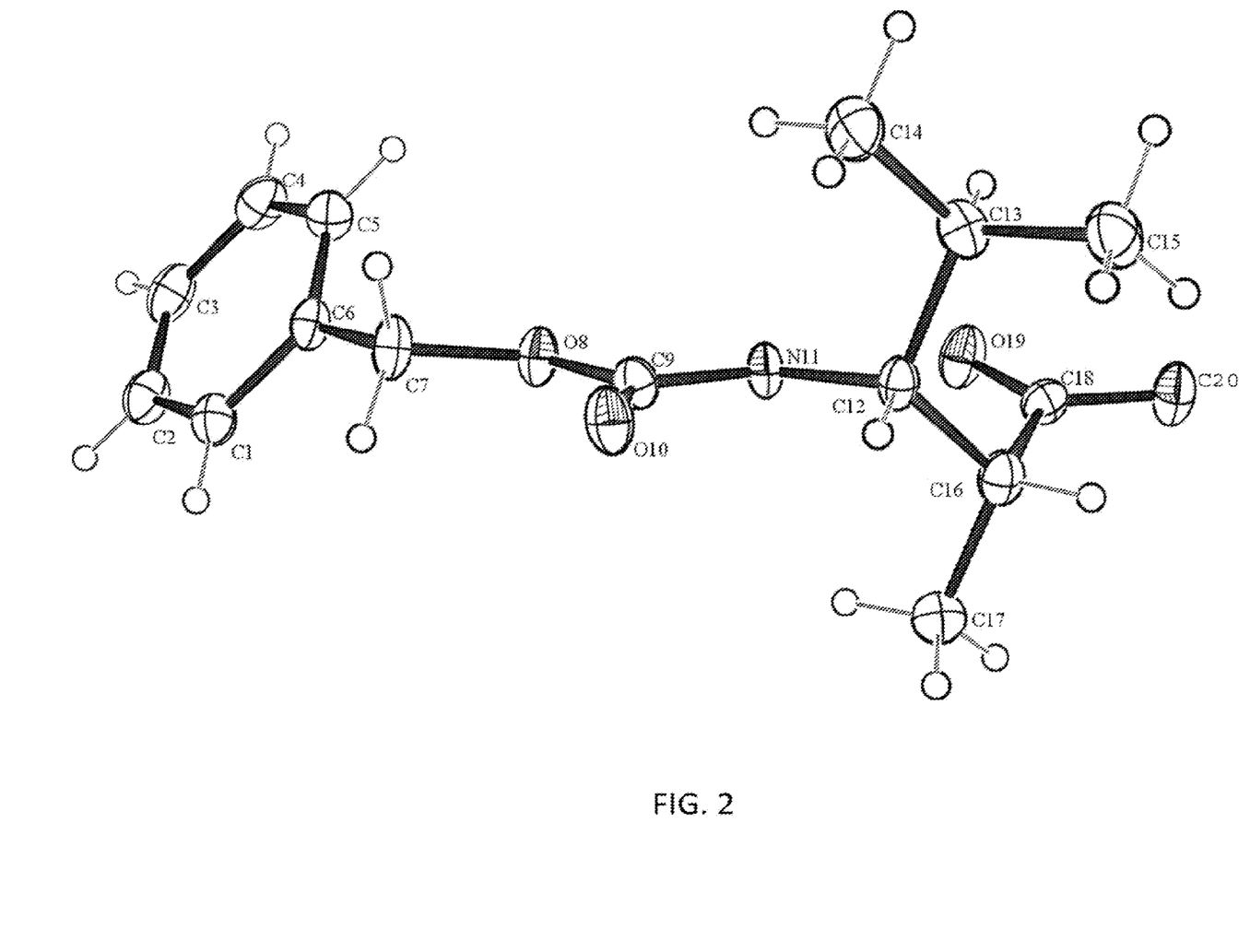
FIG. 2 is an X-ray structure of N—Z-dolamethylleuine. Atoms are displayed as 30% probability thermal ellipsoids.

The crystal structure of Z-dolamethylleuine is presented in FIG. 2. X-ray crystallographic analysis of Z-dolamethylleuine has confirmed it has the 2R, 3R configuration.

The present invention also provides a method for obtaining a crystal of Z-dolamethylleuine. The method comprises the steps of:
(a) combining Z-dolamethylleuine with a crystallization solution to produce a crystallizable composition; and
(b) subjecting the crystallizable composition to conditions that promote crystallization, thereby obtaining said crystal.

The crystallization solution comprises 2-propanol and water.

According to one embodiment, the crystallizable composition comprises Z-dolamethylleuine. Z-dolamethylleuine may be obtained by the synthetic methods described above. Z-dolamethylleuine is preferably from about 85% to about 100% pure prior to forming the composition. More preferably, Z-dolamethylleuine is about 90% to about 100% pure. Even more preferably, Z-dolamethylleuine is about 95% to about 100% pure.

Conditions that promote crystallization are known to those of skill in the art and include, but are not limited to, pH, ionic strength, temperature, Z-dolamethylleuine concentration, the presence of various salts, ligands or additives, the type of precipitant and the actual crystallization method (hanging drop, sitting drop, dialysis, etc.).

The crystallizable composition is left to stand at about 0° C. or ambient temperature for a time ranging from about one to seven days.

It would be readily apparent to one of skill in the art to vary the crystallization conditions disclosed above to identify other crystallization conditions that would produce crystals of Z-dolamethylleuine. Such variations include, but are not limited to, adjusting pH, concentration and/or crystallization temperature, introducing a salt and/or precipitant, using a device for promoting crystallization, microseeding, using a different method for crystallization, or introducing additives such as detergents (e.g., TWEEN® 20 (monolaurate), LDOA, BRIJ® 30 (4 lauryl ether)), sugars (e.g., glucose, maltose), organic compounds (e.g., dioxane, dimethylformamide), lanthanide ions, or poly-ionic compounds that aid in crystallizations. High throughput crystallization assays may also be used to assist in finding or optimizing the crystallization condition.

In some embodiments, the method for obtaining a crystal of Z-dolamethylleuine further comprises isolating the resulting crystals from the crystallizable composition. The crystals may be isolated by any conventional means, such as filtration, concentration, centrifugation, and the like.

Synthesis of TFA-Dolaphenvaline and X-Ray Structural Determination of the Same

The present invention provides a process for preparing TFA-dolaphenvaline:

The method comprises the steps of:

(a) condensing N-trifluoroacetylglycine 11 with alcohol 12 to provide allylic ester 13:

(b) converting allylic ester 13 to γ,δ-unsaturated amino acid 14:

(c) converting γ,δ-unsaturated amino acid 14 to t-butyl ester 16:

(d) oxidizing t-butyl ester 16 to t-butyl ester ketone 18:

(e) converting t-butyl ester ketone 18 to lactone 19:

and (f) converting lactone 19 to TFA-dolaphenvaline 20:

In step (a), N-trifluoroacetylglycine 11 is condensed with alcohol 12 to provide allylic ester 13. Methods for condensing a carboxylic acid with an alcohol are well known in the art and any such method may be used. In preferred embodiments, the condensation reaction uses a carbodiimide. Preferably, the carbodiimide is N,N'-dicyclohexylcarbodiimide (DCC). The condensation reaction preferably contains a catalyst, such as 4-dimethylaminopyridine (DMAP).

In step (b), allylic ester 13 is converted to γ,δ-unsaturated amino acid 14 via a Claisen rearrangement with a strong base, such as lithium bis(trimethylsilyl)amide (LHMDS) in the presence of aluminum isopropoxide (Al(O-i-Pr)$_3$) and quinidine.

In step (c), γ,δ-unsaturated amino acid 14 is converted to t-butyl ester 16. The t-butyl ester 16 may be prepared by reaction of the γ,δ-unsaturated amino acid 14 with tert-butyl acetoacetate and a catalytic amount of an acid, such as $H_2SO_4$.

In step (d), t-butyl ester 16 is oxidized to provide t-butyl ester ketone 18 using a two-step procedure with $OsO_4$ and N-methylmorpholine N-oxide (NMO) followed by $NaIO_4$.

In step (e), t-butyl ester ketone 18 is converted to lactone 19 via reductive oxygenation and cyclization of an intermediate alcohol. Methods for reductive oxygenation are known in the art and include reaction with sodium cyanoborohydride and zinc iodide.

In step (f), lactone 19 is converted to TFA-dolaphenvaline 20 via transfer hydrogenolysis. Methods for transfer hydrogenolysis are known in the art and any such method may be used. Preferably, the method uses 1,4-cyclohexadiene-Pd/C.

Scheme 2 depicts a preferred process of the present invention.

Scheme 2.

20
86%

The steps illustrated in Scheme 2 may be described as follows. DCC/DMAP-mediated condensation of N-trifluoroacetylglycine 11 with 12 (Duboudin, J. G.; Jousseaume, B.; Saux, A. *J. Organomet. Chem.* 1979, 168, 1-11) provided allylic ester 13. Claisen rearrangement of 13 with LHMDS in the presence of Al(O-i-Pr)$_3$ and quinidine afforded the γ,δ-unsaturated amino acid 14.

Reaction of 14 with tert-butyl acetoacetate and a catalytic amount of H$_2$SO$_4$ in a sealed vessel gave tert-butyl ester 16 as a crystalline solid (Taber, D. F.; Gerstenhaber, D. A.; Zhao, X. *Tetrahedron Lett.* 2006, 47, 3065-3066). tert-Butyl ester 16 was subjected to oxidative cleavage of the double bond by reaction with OsO$_4$ and NMO followed by NaIO$_4$ and yielded 18 as a crystalline solid (Keck, G. E.; Giles, R. L.; Cee, V. J.; Wager, C. A.; Yu, T.; Kraft, M. B. *J. Org. Chem.* 2008, 73, 9675-9691). With the tert-butyl ester ketone 18 in hand, the NaCNBH$_3$/ZnI$_2$ deoxygenation was attempted (Lau, C. K.; Dufresne, C.; Belanger, P. C.; Piétré, S.; Scheigetz, J. *J. Org. Chem.* 1986, 51, 3038-3043). The lactone mixture 19 was the main product. However, since the epimeric lactones 19 were an intermediate reduction product, the reductive process was completed via transfer hydrogenolysis of 19 with 1,4-cyclohexadiene-Pd/C to afford TFA-dolaphenvaline 20.

In one embodiment, the present invention provides a crystallizable composition or a crystal comprising TFA-dolaphenvaline. In another embodiment, the crystal is in space group P 1 21 1; and has unit cell dimensions of a=7.9918 (5) Å, b=6.3850 (5) Å, c=13.4458 (11) Å, α=90°, β=103.1810 (10)°, γ=90°, V=668.03 (9) Å$^3$. It will be readily apparent to those skilled in the art that the unit cells of the crystal compositions may deviate +/−1-2 Å from the above cell dimensions depending on the deviation in the unit cell calculations.

Figure 3:
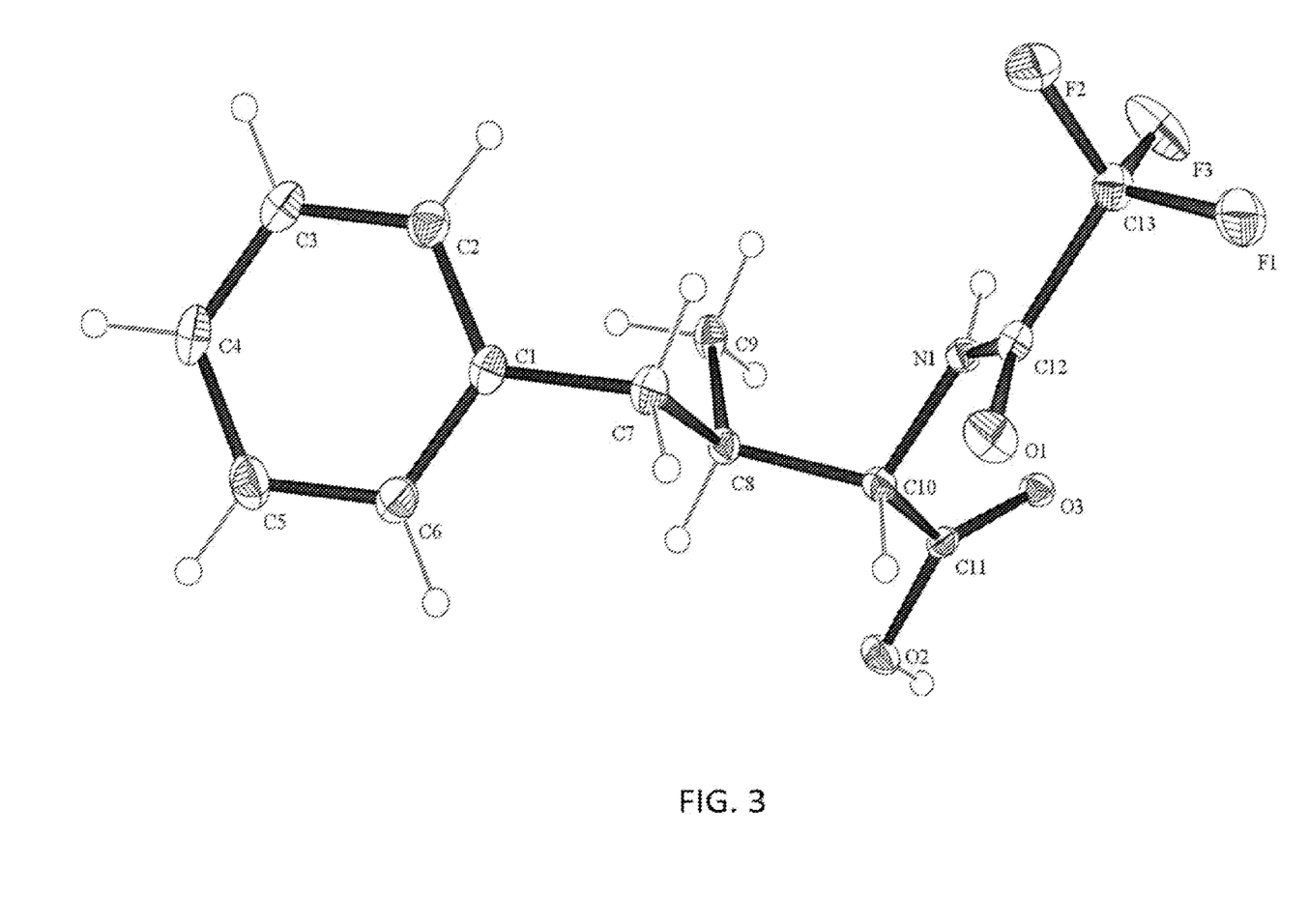
FIG. 3 is an X-ray structure of N-trifluoroacetyldolaphenvaline. Atoms are displayed as 30% probability thermal ellipsoids.

The crystal structure of TFA-dolaphenvaline is presented in FIG. 3. X-ray crystallographic analysis of TFA-dolaphenvaline has confirmed it has the 2S, 3R configuration.

The present invention also provides a method for obtaining a crystal of TFA-dolaphenvaline. The method comprises the steps of:
(a) combining TFA-dolaphenvaline with a crystallization solution to produce a crystallizable composition; and
(b) subjecting the crystallizable composition to conditions that promote crystallization, thereby obtaining said crystal.

The crystallization solution comprises methylene chloride and hexane.

According to one embodiment, the crystallizable composition comprises TFA-dolaphenvaline. TFA-dolaphenvaline may be obtained by the synthetic methods described above. TFA-dolaphenvaline is preferably from about 85% to about 100% pure prior to forming the composition. More preferably, TFA-dolaphenvaline is about 90% to about 100% pure. Even more preferably, TFA-dolaphenvaline is about 95% to about 100% pure.

Conditions that promote crystallization are known to those of skill in the art and include, but are not limited to, pH, ionic strength, temperature, TFA-dolaphenvaline concentration, the presence of various salts, ligands or additives, the type of precipitant and the actual crystallization method (hanging drop, sitting drop, dialysis, etc.).

The crystallizable composition is left to stand at about 0° C. for a time ranging from about one to seven days.

It would be readily apparent to one of skill in the art to vary the crystallization conditions disclosed above to identify other crystallization conditions that would produce crystals of TFA-dolaphenvaline. Such variations include, but are not limited to, adjusting pH, concentration and/or crystallization temperature, introducing a salt and/or precipitant, using a device for promoting crystallization, microseeding, using a different method for crystallization, or introducing additives such as detergents (e.g., TWEEN® 20 (monolaurate), LDOA, BRIJ® 30 (4 lauryl ether)), sugars (e.g., glucose, maltose), organic compounds (e.g., dioxane, dimethylformamide), lanthanide ions, or poly-ionic compounds that aid in crystallizations. High throughput crystallization assays may also be used to assist in finding or optimizing the crystallization condition.

In some embodiments, the method for obtaining a crystal of TFA-dolaphenvaline further comprises isolating the resulting crystals from the crystallizable composition. The crystals may be isolated by any conventional means, such as filtration, concentration, centrifugation, and the like.

Computer Readable Medium, Computer Systems, and Methods of Use

The present invention also provides a non-transitory computer readable medium with crystal structural data and/or information stored thereon. As used herein, the phrase "computer readable medium" refers to storage media readable by a computer, which media may be used to store and retrieve data and software programs incorporating computer code. Exemplary computer readable media include floppy disk, CD-ROM, tape, memory (such as flash memory or system memory), hard drive, and the like.

The crystal structural data and/or information stored on the computer readable medium may be those of dolastatin 16, Z-dolamethylleuine or TFA-dolaphenvaline. Preferably, the crystal structural data and/or information is of dolastatin 16.

In some embodiments, the computer readable medium further comprises programming for displaying a three dimensional structure representative of dolastatin 16, Z-dolamethylleuine or TFA-dolaphenvaline. In some embodiments, the computer readable medium further comprises programming for designing an analog of dolastatin 16.

In another embodiment, the invention provides a system, particularly a computer system, comprising a computer readable medium. The computer system may comprise: (i) a non-transitory computer readable medium comprising data storage material encoded with the computer-readable data; (ii) a working memory for storing instructions for processing the computer-readable data; and (iii) a central-processing unit coupled to the working memory and to the computer-readable medium for processing the computer-readable data and generating structures. The computer readable medium may be any of those described above.

The computer system may further comprise a display coupled to the central-processing unit for displaying the structures. The computer system may contain one or more remote devices. The remote device may comprise any of the computer systems or computer readable medium described above. The remote device may be in a different country or jurisdiction from where the computer-readable data is received. The communication with a remote device may be via the internet, intranet, e-mail etc, or transmitted through wires or by wireless means, such as by terrestrial radio or by satellite. Typically, the communication will be electronic in nature, but some, or all, of the communication pathway may be optical, for example, over optical fibers. The data received may then be used in a computer-based method to design analogs of dolastatin 16.

Thus, according to another embodiment, the present invention provides a method for designing analogs of dolastatin 16 using the computer systems described above. In particular, the structural data and/or information of dolastatin 16 can be used to design analogs of dolastatin 16 that have a similar three dimensional shape as dolastatin 16 and that are easier to make synthetically and/or have increased biological activity. In some embodiments, the structural data and/or information can be used to determine which amino acid residues can be substituted or deleted in the chemical structure of the analogs. In other embodiments, the structural data and/or information can be used to determine whether amino acid residues can be added to the chemical structure of the analogs.

In the designed analogs of dolastatin 16, the amino acid residues that are substituted or added may be any natural or unnatural amino acid residue or amino acid analog.

In these methods, it is possible to carry out virtual modeling of dolastatin 16 and analogs thereof for analysis and optimization of their three-dimensional shape using the structural data and/or information described above. Briefly, the three-dimensional structures of the present invention are input into a computer so that images of the structure and various parameters are shown on the display. Then, the structure and various parameters can be manipulated to create virtual models of dolastatin 16 and analogs thereof, wherein the effect of at least one amino acid residue substitution, deletion, or addition on the three-dimensional shape can be analyzed. Advantageously, such analyses may be performed prior to the actual synthesis and testing of the dolastatin 16 analogs by the use of computer modeling techniques.

Computer modeling techniques and specialized computer programs used in designing analogs are known to those of skill in the art and any such technique or program may be used.

In order that this invention be more fully understood, the following examples are set forth. These examples are for the purpose of illustration only and are not to be construed as limiting the scope of the invention in any way.

EXAMPLES

General Experimental Procedures

All starting reagents were used as purchased unless otherwise stated. Reactions were monitored by TLC on Analtech silica gel GHLF uniplates visualized under long- and short-wave UV irradiation and stained with $H_2SO_4$/heat, phosphomolybdic acid/heat, or $KMnO_4$/heat. Solvent extracts were dried over anhydrous sodium sulfate. Where appropriate, the crude products were separated by flash chromatography on silica gel (230-400 mesh ASTM) from E. Merck.

Melting points were uncorrected and were determined employing an Electrothermal Mel-Temp apparatus. The $^1H$ and $^{13}C$ NMR spectra were recorded employing Varian Gemini 300, Varian Unity 400, or Varian Unity 500 instruments in $CDCl_3$ unless otherwise indicated. HRMS data were recorded with a JEOL LCmate or JEOL GCmate mass spectrometer. Elemental analyses were determined by Galbraith Laboratories, Inc., Knoxville, Tenn. X-ray structure analyses were performed on a Bruker AXS Smart 600 diffractometer. The X-ray data have been submitted as supplemental information (CCDC 801992 (1), 801990 (8), and 801991 (20) contain the supplementary crystallographic data. These data can be obtained free of charge from The Cambridge Crystallographic Data Centre via www.ccdc.cam.ac.uk/data_request/cif). Descriptions of the X-ray techniques utilized in our laboratory have been previously described (Pettit, G. R.; Knight, J. C.; Herald, D. L.; Pettit, R. K.; Hogan, F.; Mukku, V. J. R. V.; Hamblin, J. S.; Dodson, M. J., II; Chapuis, J.-C. *J. Nat. Prod.* 2009, 72, 366-371.).

1-Diazo-2-oxo-(3R)-3-benzyloxycarbonylamino-4-methylpentane (5)

A solution of Z—R-valine (4, 1.01 g, 3.98 mmol) and TEA (0.57 mL, 415 mg, 4.11 mmol) in THF (20 mL) under $N_2$ was cooled to −15° C. Ethyl chloroformate (0.39 mL, 446 mg, 4.11 mmol) in THF (4 mL) was added, and the solution stirred at −15° C. for 30 min. The solution was filtered and the precipitate washed with THF (10 mL). The combined filtrate and washings were diluted with acetonitrile (20 mL) and cooled to 0° C. under $N_2$. Trimethylsilyldiazomethane (4 mL of a 2 M solution in hexane, 8 mmol) was added, and the solution stirred at ambient temperature for 18 h. The reaction mixture was diluted with ether (80 mL), washed successively with 10% citric acid (50 mL), saturated $NaHCO_3$ (50 mL), and 5 M NaCl (20 mL), dried, evaporated, and coevaporated with toluene (15 mL). The residue was separated by chromatography on silica gel (30 g, 7:3 hexane-EtOAc) to afford 0.37 g (34%) of 5 as a pale yellow solid: mp 68-69° C.; $R_f$ 0.21 (4:1 hexane-EtOAc); $[\alpha]^{23}_D$+25 (c 1.10, $CHCl_3$); $^1H$ NMR δ 7.33 (5H, m), 5.39 (2H, br s), 5.11 (2H, s), 4.13 (1H, m), 2.09 (1H, heptet), 0.99 (3H, d), 0.89 (3H, d); anal. C, 61.31, H, 6.56, N, 14.93%, calcd for $C_{14}H_{17}N_3O_3$, C, 61.08, H, 6.22, N, 15.26%.

tert-Butyl (3S)-3-Z-amino-4-methylpentanoate (6)

Diazo-derivative 5 (0.602 g, 2.19 mmol) was dissolved in t-BuOH (9 mL) under $N_2$ at 70° C. Silver benzoate (80.2 mg, 0.35 mmol) in TEA (0.94 mL, 685 mg, 6.70 mmol) was added dropwise, and the mixture stirred at 70° C. in the dark for 4 h. The mixture was allowed to cool and was filtered through Celite, and the solvent was evaporated. The residue was partitioned between EtOAc (100 mL) and saturated $NaHCO_3$ (20 mL). The organic phase was separated, washed with saturated $NaHCO_3$ (20 mL), $H_2O$ (20 mL), and 5 M NaCl (20 mL), and dried, and the solvent was evaporated. The residue was chromatographed (silica gel, 23 g; 9:1 hexane-acetone) to provide 0.443 g (63%) of 6 as a colorless oil: $R_f$ 0.46 (5:1 hexane-acetone); $[\alpha]^{23}_D$+22 (c 1.20, $CHCl_3$); $^1H$ NMR δ 7.34 (5H, m), 5.12 (1H, d), 5.09 (2H, s), 3.81 (1H, qt), 2.45 (1H, dd, J=5, 15 Hz), 2.37 (1H, dd, J=7, 15 Hz), 1.81 (1H, m), 1.42 (9H, s), 0.93 (3H, d, J=3 Hz), 0.91 (3H, d, J=3 Hz); $^{13}$C NMR δ 170.5, 155.5, 136.2, 127.9, 127.5, 80.4, 66.0, 53.3, 37.9, 31.5, 27.5, 18.7, 18.0; HRMS m/z 322.2041 [M+H]$^+$ (calcd for $C_{18}H_{28}NO_4$, 322.2018); anal. C, 67.05, H, 8.44, N, 4.40%, calcd for $C_{18}H_{27}NO_4$, C, 67.26, H, 8.47, N, 4.36%.

tert-Butyl (2R,3R)-3-N—Z-amino-2,4-dimethylpentanoate (7)

To a stirred mixture of dipyridyl indicator, LiCl (0.77 g, 18 mmol), and diisopropylamine (2.0 mL, 14 mmol), in THF at −78° C. under $N_2$ was added BuLi (1.6 M soln in hexane, 8.75 mL, 14 mmol) dropwise until the mixture turned a wine-red color. The mixture was stirred at −78° C. for 15 min, and 6 (1.90 g, 5.9 mmol) in THF (15 mL) was added. The reaction mixture was stirred for 1 h, followed by the addition of iodomethane (1.9 mL, 31 mmol). Stirring was continued for 21 h at ambient temperature. The reaction was terminated by the addition of saturated $NH_4Cl$ (30 mL), and the mixture was extracted with EtOAc (150 mL). The extract was washed with 10% $Na_2S_2O_3$ (30 mL), and the washing was back-extracted with EtOAc (100 mL). The organic solutions were combined, dried and evaporated. The residue was further separated by chromatography on silica gel (60 g, 9:1 hexane-acetone) to yield 1.60 g (80%) of 7 as a colorless oil: $R_f$ 0.44 (9:1 hexane-acetone); $[\alpha]^{23}_D$+22 (c 0.70, $CHCl_3$); $^1$H NMR δ 7.33 (5H, m), 5.62 (1H, d, J=7.2 Hz), 5.10 (2H, s), 3.44 (1H, m), 2.66 (1H, m), 1.71 (1H, m), 1.42 (9H, s), 1.18 (3H, d, J=7.2 Hz), 0.96 (3H, d, J=6.6 Hz), 0.92 (3H, d, J=6.6 Hz); $^{13}$C NMR δ 174.6, 156.4, 136.4, 127.9, 80.3, 65.9, 59.0, 40.7, 31.4, 27.5, 19.3, 18.7, 15.3; HRMS m/z 336.2155 [M+H]$^+$ (calcd for $C_{19}H_{30}NO_4$, 336.2175); anal. C, 68.16, H, 8.91, N, 4.47%, calcd for $C_{19}H_{29}NO_4$, C, 68.03, H, 8.71, N, 4.18%.

(2R,3R)-3-Z-amino-2,4-dimethylpentanoic Acid (8)

To a solution of 7 (1.6 g, 4.8 mmol) in DCM (9.9 mL) under $N_2$ was added a mixture of trifluoroacetic acid (4.6 mL, 62 mmol) and triethylsilane (1.9 mL, 12 mmol). Stirring was continued for 4 h at ambient temperature. Solvents were removed and the residue coevaporated with toluene (2×30 mL). The residue was dissolved in EtOAc (100 mL) and extracted with 6% $NaHCO_3$ (4×40 mL). The aqueous extracts were combined, acidified (pH 2) with 6 N HCl, and extracted with EtOAc (3×40 mL). The organic extracts were combined, washed with 5 M NaCl (20 mL), dried, and evaporated to provide a colorless solid that crystallized from 2-propanol-water to provide Z-Dml (8, 1.0 g, 77%) as colorless crystals: mp 135° C.; $R_f$ 0.59 (50:50:1 hexane-acetone-HOAc); $[\alpha]^{25}_D$+35 (c 0.86, $CHCl_3$); $^1$H NMR δ 7.34 (5H, m), 5.61 (1H, J=10.5 Hz), 5.11 (2H, s), 3.46 (1H, m), 2.83 (1H, m), 1.77 (1H, m), 1.25 (3H, d, J=7.2 Hz), 0.96 (3H, d, J=6.6 Hz), 0.93 (3H, d, J=6.6 Hz); $^{13}$C NMR δ 179.4, 156.6, 136.2, 127.9, 127.5, 127.4, 66.1, 58.8, 39.8, 19.4, 18.8, 15.3; HRMS m/z 280.1558 [M+H]$^+$ (calcd for $C_{15}H_{22}NO_4$, 280.1549); anal. C, 64.69, H, 7.73, N, 4.96%, calcd for $C_{15}H_{21}NO_4$, C, 64.50, H, 7.58, N, 5.01%.

(E)-2-Phenylbut-2-enyl 2-(2,2,2-Trifluoroacetamido) acetate (13)

To a suspension of N-trifluoroacetylglycine (11, 3.68 g, 21.50 mmol) and (E)-2-phenyl-2-buten-1-ol (12, 2.68 g, 19.32 mmol) in DCM (60 mL) at −40° C. under $N_2$ was added via cannula a solution of dicyclohexylcarbodiimide (4.43 g, 21.50 mmol) and 4-dimethylaminopyridine (0.269 g, 2.15 mmol) in DCM (60 mL). The solution was stirred at ambient temperature for 18 h and filtered, and the precipitate was washed with DCM (2×40 mL). The combined filtrate and washing was washed with 10% citric acid (2×25 mL), $H_2O$ (10 mL), 6% $NaHCO_3$ (2×25 mL), and 5 M NaCl (20 mL), and dried, and the solvent was evaporated. The residue was chromatographed (silica gel, 150 g; 4:1 hexane-EtOAc) to afford 5.06 g (87%) of 13 as a pale yellow oil that solidified on standing: mp 49-50° C.; $R_f$ 0.66 (4:1 hexane-EtOAc); $^1$H NMR δ 7.37 (2H, t, J=7.5 Hz), 7.30 (1H, t, J=7.2 Hz), 7.18 (2H, d, J=7.6 Hz), 6.75 (1H, br s), 5.95 (1H, q, J=6.9 Hz), 4.91 (2H, s), 4.06 (2H, d, J=4.9 Hz), 1.66 (3H, d, J=6.9 Hz); $^{13}$C NMR δ 167.9, 156.7 (m), 137.3, 135.4, 135.4, 128.5, 128.4, 127.4, 116.9, 70.8, 41.4, 14.6; MS APCI$^+$ m/z 302.1026 [M+H]$^+$ (calcd for $C_{14}H_{15}F_3NO_3$, 302.1004); anal. C, 55.73, H, 4.93, N, 4.67%, calcd for $C_{14}H_{14}F_3NO_3$, C, 55.82, H, 4.68, N, 4.65%.

3-Methyl-4-phenyl-2-(2,2,2-trifluoroacetamido)-(2S,3R)-pent-4-enoic Acid (14)

To a solution of hexamethyldisilazane (6.19 g, 8.0 mL, 38.5 mmol) in THF (20 mL at −20° C. under $N_2$) was added BuLi (1.6 M solution in hexane, 20 mL, 32 mmol). The solution was stirred at −20° C. for 20 min and added via cannula to a suspension of 13 (2.00 g, 6.64 mmol), quinidine (4.30 g, 13.27 mmol), and aluminum isopropoxide (2.04 g, 10.0 mmol) in THF (70 mL) at −78° C. The solution was allowed to come to ambient temperature, and stirring was continued for 18 h. The mixture was next diluted with EtOAc (250 mL) and washed with 1 N HCl (3×75 mL). The combined washings were extracted with EtOAc (50 mL). The organic solutions were combined and extracted with 6% $NaHCO_3$ (7×50 mL). The aqueous extracts were combined, cooled in an ice bath, acidified (pH 1) with 6 N HCl, and extracted with EtOAc (4×50 mL). The organic extracts were combined, washed with 5 M NaCl (20 mL), dried, and evaporated to give 1.54 g (77%) of 14 as a pale yellow semi-solid: $R_f$ 0.76 (95:5:1 DCM-$CH_3OH$—HOAc); $^1$H NMR δ 9.10 (1H, br), 7.33 (5H, m), 6.42 (1H, d, J=8.2 Hz), 5.37 (1H, m), 5.15 (1H, s), 4.68 (1H, dd, J=8.6 and 3.4 Hz), 3.57 (1H, m), 1.31 (3H, d, J=7.2 Hz); $^{13}$C NMR δ 174.8, 156.6 (m), 148.6, 140.8, 128.6, 128.2, 126.7, 115.1, 55.0, 39.5, 14.0; MS APCI$^+$ m/z 302.1010 [M+H]$^+$, (calcd for $C_{14}H_{15}F_3NO_3$, 302.1004).

Methyl 3-Methyl-4-phenyl-2-(2,2,2-trifluoroacetamido)-(2S,3R)-pent-4-enoate (15)

Carboxylic acid 14 (544.4 mg, 1.81 mmol) was placed in 1:1 $CH_3OH$-toluene (6 mL) under $N_2$, and trimethylsilyldiazomethane (2 M solution in hexane, 4.0 mL, 8.0 mmol) was added. The solution was stirred at ambient temperature for 16 h. The solvent was evaporated, and the residue was chromatographed (silica gel, 17 g; 9:1 hexane-EtOAc) to yield 0.46 g (81%) of 15 as a colorless oil: $R_f$ 0.54 (4:1 hexane-EtOAc); $^1$H NMR δ 7.33 (5H, m), 6.48 (1H, br d), 5.34 (1H, s), 5.11 (1H, d, J=0.8 Hz), 4.64 (1H, dd, J=8.7 and 4.0 Hz), 3.76 (3H, s), 3.48 (1H, m), 1.26 (3H, d, J=7.1 Hz).

tert-Butyl 3-Methyl-4-phenyl-2-(2,2,2-trifluoroacetamido)-(2S,3R)-pent-4-enoate (16)

To carboxylic acid 14 (1.54 g, 5.12 mmol) in a 50 mL round-bottom flask was added tert-butyl acetoacetate (5.8 mL, 5.53 g, 34.97 mmol) and $H_2SO_4$ (43.1 mg, 0.44 mmol). The flask was tightly stoppered, and the solution was stirred at ambient temperature under $N_2$ for 20 h. The mixture was cooled (ice) before dilution with EtOAc (100 mL). The organic solution was washed with 6% NaHCO$_3$ (4×20 mL) and 5 M NaCl (10 mL), and dried, and the solvent was evaporated. The NaHCO$_3$ washings were combined, acidified (pH 1) with 6 N HCl, and extracted with EtOAc (3×15 mL). The extracts were combined, washed with 5 M NaCl (10 mL), and dried, and the solvent was evaporated to afford 0.65 g (42%) of 14. The neutral residue was chromatographed (silica gel, 30 g, 95:5 hexane-EtOAc) and led to 1.06 g (58%, 100% based on recovered starting material) of 16 as a colorless solid: mp 108° C.; R$_f$ 0.50 (95:5 hexane-EtOAc); $[\alpha]^{23}_D$ 25.2 (c 1.04, CH$_3$OH); $^1$H NMR δ 7.34 (5H, m), 6.48 (1H, br d, J=6.8 Hz), 5.33 (1H, s), 5.10 (1H, s), 4.52 (1H, dd, J=8.4 and 3.5 Hz), 3.47 (1H, m), 1.49 (9H, s), 1.27 (3H, d, J=7.0 Hz); $^{13}$C NMR δ 168.8, 156.5 (m), 149.0, 141.3, 128.5, 127.9, 126.8, 114.7, 83.3, 55.6, 39.9, 28.0, 14.3; MS APCI$^+$ m/z 358.1681 (0.6) [M+H]$^+$ (calcd for C$_{18}$H$_{23}$F$_3$NO$_3$, 358.1630), 302.0990 (100) [M+H−C$_4$H$_8$]$^+$ (calcd for C$_{14}$H$_{15}$F$_3$NO$_3$, 302.1004); anal. C, 60.14, H, 6.41, N, 3.96%, calcd for C$_{18}$H$_{22}$F$_3$NO$_3$, C, 60.50, H, 6.21, N, 3.92%.

tert-Butyl 3-Methyl-4-oxo-4-phenyl-2-(2,2,2-trifluoroacetamido)-(2S,3R)-butanoate (18)

To olefin 16 (903.4 mg, 2.53 mmol) in THF (25 mL) under N$_2$ was added NMO (60% wt solution in H$_2$O, 0.90 mL, 5.06 mmol) and OsO$_4$ (4% wt solution in H$_2$O, 1.50 mL, 0.25 mmol). The solution was stirred at ambient temperature for 16 h, and NaIO$_4$ (2.16 g, 10.12 mmol) was then added, followed by H$_2$O (2.7 mL). Stirring was continued for 4 h, and the reaction mixture was then diluted with EtOAc (200 mL) and washed with 10% Na$_2$S$_2$O$_3$ (4×50 mL). The combined washings were extracted with EtOAc (50 mL). The organic solutions were combined and washed with 5 M NaCl (20 mL) and dried, and the solvent was evaporated. The residue was separated by chromatography (silica gel, 30 g; 9:1 hexane-EtOAc) and led to 0.632 g (70%) of 18 as a colorless solid: mp 127-128° C.; R$_f$ 0.19 (95:5 hexane-EtOAc); $[\alpha]^{23}_D$ −39.0 (c 1.05, CH$_3$OH); $^1$H NMR δ 7.92 (2H, dd, J=7.5 and 1.3 Hz), 7.60 (1H, tt, J=7.5 and 1.3 Hz), 7.49 (2H, t, J=7.6 Hz), 7.03 (1H, br d, J=6.7 Hz), 4.72 (1H, dd, J=7.4 and 4.8 Hz), 4.13 (1H, m), 1.49 (9H, s), 1.36 (3H, d, J=7.2 Hz); $^{13}$C NMR δ 200.0, 168.3, 156.9 (q), 135.5, 133.6, 128.8, 128.4, 83.8, 55.0, 42.9, 27.8, 14.2; MS APCI$^+$ m/z 360.1417 [M+H]$^+$ (calcd for C$_{17}$H$_{21}$F$_3$NO$_4$, 360.1423); anal. C, 56.39%, H, 5.60%, N, 3.96%, calcd for C$_{17}$H$_{20}$F$_3$NO$_4$, C, 56.82%, H, 5.61%, N, 3.90%.

3-N-(2',2',2'-Trifluoroacetamido)-4-methyl-2-oxo-5-phenyl-(3S,4S)-tetrahydrofuran (19)

To ketone 18 (331.2 mg, 0.92 mmol) in 1,2-dichloroethane (5.0 mL) under N$_2$ were added ZnI$_2$ (440.2 mg, 1.38 mmol) and NaCNBH$_3$ (434.7 mg, 6.90 mmol). The mixture was stirred at 75° C. for 16 h, quenched with 9:1 saturated NH$_4$Cl-6 N HCl (20 mL), and extracted with EtOAc (3×15 mL). The extracts were combined, washed successively with 6% NaHCO$_3$ (2×15 mL) and 5 M NaCl (10 mL), and dried. After evaporation of solvent, the residue was chromatographed (silica gel, 10 g; 4:1 hexane-EtOAc) to afford 0.123 g (47%) of 19 as a white, waxy solid: R$_f$ 0.32 (4:1 hexane-EtOAc); $^1$H NMR δ 7.37 (5H, m), 7.14 (1H, br d), 5.61 (0.33H, d, J=8.4 Hz), 4.99 (0.67H, d, J=10.2 Hz), 4.68 (1H, m), 2.99 (0.33H, m), 2.59 (0.67H, m), 1.22 (0.67H, d, J=6.6 Hz), 0.87 (0.33H, d, J=6.9 Hz); HRMS (APCI$^+$) m/z 288.0851 [M+H]$^+$ (calcd for C$_{13}$H$_{13}$F$_3$NO$_3$, 288.0848).

(2S,3R)-2-(2,2,2-Trifluoroacetamido)-3-methyl-4-phenyl-2-butanoic Acid (20)

To lactone 19 (74.7 mg, 0.26 mmol) in CH$_3$OH (2.0 mL) under N$_2$ (cooled to 0° C.) was added 10% Pd/C (75 mg), followed by 1,4-cyclohexadiene (0.21 g, 2.60 mmol), and the mixture was stirred at ambient temperature under N$_2$ for 4 h. The reaction mixture was diluted with CH$_3$OH (10 mL), and the solution was filtered through Celite. The filter cake was washed with CH$_3$OH (10 mL). The solvent was evaporated from the combined filtrate and washings, and the residue was dissolved in EtOAc (20 ml) and extracted with 6% NaHCO$_3$ (3×15 mL). The organic phase was washed with 5 M NaCl (10 mL) and dried, and removal of solvent gave 48.5 mg of recovered lactone 19. The NaHCO$_3$ extracts were combined, acidified (pH 1) with 6 N HCl, and extracted with EtOAc (3×15 mL). The extracts were combined, washed with 5 M NaCl (10 mL), and dried, and the solvent was evaporated to afford 22.7 mg (86% based on recovered starting material) of 20 as a white solid: mp 122° C.; R$_f$ 0.38 (97.5:2.5:0.5 DCM-CH$_3$OH—HOAc); $[\alpha]_D^{25}$+24.2 (c 1.49, CH$_3$OH); $^1$H NMR δ 9.78 (1H, br), 7.31 (2H, t, J=7.3 Hz), 7.23 (1H, t, J=7.3 Hz), 7.17 (2H, d, J=7.1 Hz), 6.64 (1H, d, J=8.4 Hz), 4.75 (1H, dd, J=8.8 and 3.2 Hz), 2.76 (1H, dd, J=12.9 and 6.0 Hz), 2.55 (1H, m), 2.49 (1H, dd, J=13.1 and 8.0 Hz), 0.99 (3H, d, J=6.6 Hz); $^{13}$C NMR δ 175.23, 157.17 (m), 138.58, 128.96, 128.64, 126.71, 115.60 (m), 55.73, 39.64, 37.85, 14.84; MS APCI$^-$ m/z 288.0835 [M−H]$^-$ (calcd for C$_{13}$H$_{13}$F$_3$NO$_3$, 288.0845); anal. C, 53.15, H, 4.69, N, 4.70%, calcd for C$_{13}$H$_{14}$F$_3$NO$_3$.0.2 H$_2$O, C, 53.32, H, 4.96, N, 4.78%.

While particular materials, formulations, operational sequences, process parameters, and end products have been set forth to describe and exemplify this invention, they are not intended to be limiting. Rather, it should be noted by those ordinarily skilled in the art that the written disclosures are exemplary only and that various other alternatives, adaptations, and modifications may be made within the scope of the present invention. Accordingly, the present invention is not limited to the specific embodiments illustrated herein, but is limited only by the following claims.

What is claimed is:

1. A crystal comprising dolastatin 16:

wherein said crystal is in space group P2(1); and said crystal has unit cell dimensions of a=10.844 (5) Å, b=16.133 (5) Å, c=16.050 (5) Å, α=90.000 (5°), β=104.062 (5°), γ=90.000 (5°), V=2720.4 (17) Å$^3$.

2. A crystallizable composition comprising dolastatin 16, wherein the crystallizable composition forms a crystal of dolastatin 16 that is of X-ray diffraction quality and wherein said crystal is in space group P2(1); and said crystal has unit cell dimensions of a=10.844 (5) Å, b=16.133 (5) Å, c=16.050 (5) Å, α=90.000 (5°), β=104.062 (5°), γ=90.000 (5°), V=2720.4 (17) Å$^3$.

3. A crystal of dolastatin 16 having the X-ray crystal structure of FIG. 1 and wherein said crystal is in space group P2(1); and said crystal has unit cell dimensions of a=10.844 (5) Å, b=16.133 (5) Å, c=16.050 (5) Å, α=90.000 (5°), β=104.062 (5°), γ=90.000 (5°), V=2720.4 (17) Å$^3$.

4. A method of obtaining a crystal of dolastatin 16, wherein said crystal is in space group P2(1); and said crystal has unit cell dimensions of a=10.844 (5) Å, b=16.133 (5) Å, c=16.050 (5) Å, α=90.000 (5°), β=104.062 (5°), γ=90.000 (5°), V=2720.4 (17) Å$^3$, the method comprising the steps of:
  (a) combining dolastatin 16 with a crystallization solution to produce a crystallizable composition; and
  (b) subjecting the crystallizable composition to conditions that promote crystallization, thereby obtaining said crystal.

* * * * *